United States Patent [19]

Arima et al.

[11] Patent Number: 4,481,499

[45] Date of Patent: Nov. 6, 1984

[54] GAS DETECTOR

[75] Inventors: Hideo Arima; Masayoshi Kaneyasu, both of Yokohama; Mitsuko Ito, Yokosuka, all of Japan

[73] Assignee: Hitachi, Ltd., Tokyo, Japan

[21] Appl. No.: 489,179

[22] Filed: Apr. 27, 1983

[30] Foreign Application Priority Data

May 7, 1982 [JP] Japan .................................. 57-75096

[51] Int. Cl.³ ........................ G01N 27/04; H01L 7/00
[52] U.S. Cl. ......................................... 338/34; 73/23; 73/27 R; 422/94; 422/98
[58] Field of Search ................... 338/34; 73/23, 27 R; 422/94, 98; 340/623

[56] References Cited

U.S. PATENT DOCUMENTS

| | | |
|---|---|---|
| 3,644,795 | 2/1972 | Taguchi ............................ 338/34 X |
| 3,695,848 | 10/1972 | Taguchi .......................... 340/634 X |
| 3,951,603 | 4/1976 | Obayashi et al. ................. 338/34 X |
| 4,001,756 | 1/1977 | Heijne ..................................... 338/34 |
| 4,033,169 | 7/1977 | Fujishiro et al. ................. 338/34 X |
| 4,039,941 | 8/1977 | Morrison .......................... 338/34 X |
| 4,223,550 | 9/1980 | Takahama et al. ..................... 73/23 |
| 4,224,280 | 9/1980 | Takahama et al. ................. 73/23 X |
| 4,322,968 | 4/1982 | Takami et al. ...................... 73/27 R |
| 4,351,182 | 9/1982 | Schmidberger ..................... 73/27 R |

*Primary Examiner*—C. L. Albritton
*Assistant Examiner*—Christopher N. Sears
*Attorney, Agent, or Firm*—Antonelli, Terry & Wands

[57] ABSTRACT

A gas detector with a layer of gas sensing material comprising an oxide semiconductor, wherein at least one coating layer each of a p-type oxide semiconductor and an n-type oxide semiconductor is provided in a multi-layer arrangement on the surface of said layer of gas sensing material that contacts the gas. The gas detector can selectively identify only specific gases.

13 Claims, 4 Drawing Figures

GAS DETECTOR

BACKGROUND OF THE INVENTION

1. Field of the Invention

The present invention relates to a gas detector capable of selectively detecting different gases.

2. Brief Description of the Prior Art

The generally familiar gas sensing materials include oxide semiconductors such as $SnO_2$, $Fe_2O_3$, and $ZnO$. These oxide semiconductors are used as gas sensing materials because their resistance varies considerably with the type of gas present, making them ideal as sensing elements for detecting the presence of various gases. Unfortunately, because they cannot be used to identify the type of gas, it has been impossible to employ these for purposes other than to detect a specific gas. Accordingly, when gas detectors in which these oxide semiconductors function as the gas sensing material are used for the detection of only a specific gas, it is impossible to avoid malfunctions arising from the presence of other gases. This lowers the reliability to the user of gas detection devices employing this type of gas detector. Fed up with the constant detection of gases other than the desired gas, the user sometimes ends up by turning the device off and leaving it off. Japanese Patent Application Kokai (Laid-open) No. 53-36,296 discloses one means for overcoming this drawback in gas detectors according to the prior art. It proposes that the surface of the gas sensing material be coated with cupric oxide. However, merely coating the gas sensing material with cupric oxide was found to be inadequate for providing a gas detector with the ability to identify gases.

SUMMARY OF THE INVENTION

The object of the present invention is to provide a gas sensor capable of selectively identifying only specific gases.

In order to achieve this, the present invention provides at least one coating layer each of a p-type oxide semiconductor and an n-type oxide semiconductor on the surface of a gas sensing material consisting of an oxide semiconductor.

The inventors have discovered that gas detectors employing an n-type oxide semiconductor such as $SnO_2$ or $ZnO$ as the gas sensing material have considerable gas selectivity when a coating layer of a p-type oxide semiconductor selected from the group consisting of $NiO$, $LaNiO_3$, and $(Mn, Co, Ni, Al)_3O_4$, which has a spinel structure, is formed on the surface of this gas sensing material, and on top of this coating layer is formed another coating layer of an n-type oxide semiconductor selected from the group consisting of $SnO_2$, $WO_3$, $Ta_2O_5$, $ZnO$, $Fe_2O_3$, $TiO_2$, and $Nb_2O_5$. It has also been found that, instead of using only one layer each of the above-mentioned p-type and n-type oxide semiconductor coating layers, the alternative arrangement of successive layers in the order p-type, n-type, p-type, n-type, and so forth makes it possible to obtain a gas sensor of even better gas selectivity. Moreover, the inventors have also discovered that even when the gas sensing material consists of a p-type oxide semiconductor such as $NiO$, the gas selectivity of the gas detector can be raised by forming coating layers of the oxide semiconductors described above on the surface of this gas sensing material in the order n-type, p-type, n-type, p-type, and so forth.

EXAMPLE 1

Figure 1:
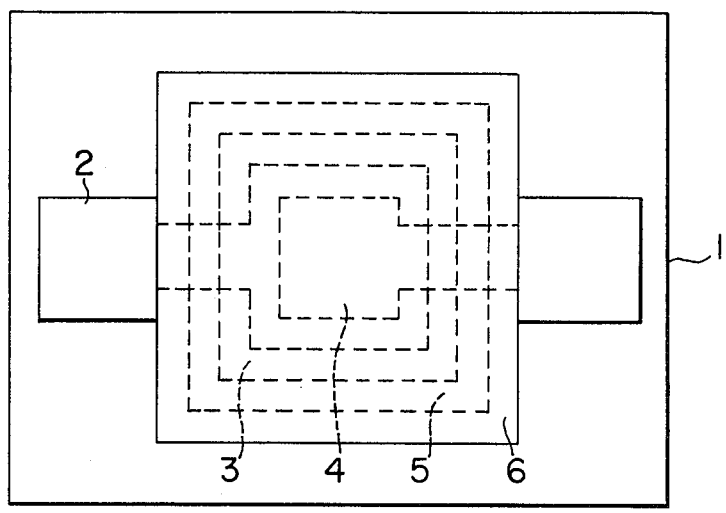
FIGS. 1 and 2 are plan and cross-sectional views of one embodiment of the gas detector in the present invention.
Figure 2:
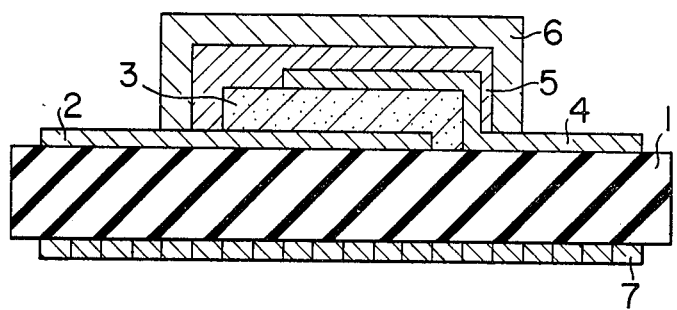

FIGS. 1 and 2 show a gas detector comprising an alumina substrate 1 on which lower electrode 2, gas sensing material layer 3, upper electrode 4, and coating layers 5 and 6 are provided in a successive sandwich-like multi-layer arrangement, said detector being provided also with a heater 7 at the bottom of alumina substrate 1. This gas detector is fabricated by means of steps (1) to (9) described below.

(1) The pattern for heater 7 is printed with a platinum paste on the bottom surface of 96%-pure alumina substrate 1, then dried. (2) The pattern for lower electrode 2 is printed with the same platinum paste on the top surface of alumina substrate 1, then dried. (3) This substrate 1 is fired for 2 hours in an electric furnace at 1200° C. to form heater 7 and lower electrode 2. (4) Gas sensing material layer 3 comprising 89%, by weight, of $SnO_2$ powder, 1% palladium powder, and 10% $PbO$—$TiO_2$—$SiO_2$ glass is printed on lower electrode 2, and dried. (5) Upper electrode 4 is printed with the same platinum paste as used for bottom electrode 2 onto said gas sensing material layer 3, then dried. (6) The partially completed gas detector is then fired for 10 minutes in a belt furnace at 900° C. to form gas sensing material layer 3 and upper electrode 4. (7) Coating layer 5 comprising 90%, by weight, of p-type oxide semiconductor, and 10% $PbO$—$TiO_2$—$SiO_2$ glass is printed upon this detector and dried. (8) On top of this is printed coating layer 6 comprising 90%, by weight, of n-type oxide semiconductor, and 10% $PbO$—$TiO_2$—$SiO_2$ glass, which is then dried. (9) The detector obtained from the preceding steps is then fired for 10 minutes in a belt oven at 900° C. to form coating layers 5 and 6 comprising p-type and n-type oxide semiconductors. When three or four layers of coating layers 5 and 6 are to be formed, steps (7) and (8) above are repeated.

FIGS. 1 and 2 show a gas detector fabricated according to the steps described above and using the n-type oxide semiconductor $SnO_2$ as the gas sensing material.

Table 1 gives the present change in resistance of the gas detector when various oxide semiconductors are used in coating layers 5 and 6.

Data Nos. 1 to 3 in Table 1 give the characteristics of conventional gas detectors and are included for comparison. The results obtained for the gas detectors represented in data Nos. 1 to 15 were obtained at a temperature of 400° C. maintained by passing current through heater 7, and at gas concentrations set at 1000 ppm. Five of each type of gas detector were provided for the tests, and the percent change between the resistance prior to gas contact and the resistance following gas contact shown for each type of gas detector in the table as an average of five values.

It is apparent from Table 1 that, compared with the conventional gas detectors (data Nos. 1 to 3) that have either one or no coating layer, the gas detectors according to the present invention (data Nos. 4 to 15) that have coating layers 5 and 6 consisting of p-type and n-type oxide semiconductors have a greatly reduced detection sensitivity (percent change in resistance is reduced) to hydrogen and ethanol gas and a greatly increased detection sensitivity to methane gas. It is clear from this that the selectivity for methane gas is greatly enhanced.

When a gas detector according to the present invention is used, for example, as a town gas detection alarm device, because the total concentration of interfering gases such as hydrogen and ethanol in ordinary town gas is at most 1000 to 2000 ppm, malfunction of the device due to hydrogen or ethanol gas can be avoided by setting the methane gas alarm level at above 2000 ppm. Since, in the case of town gas, an alarm need in general be emitted only at a methane gas concentration of no more than 12,500 ppm, the town gas detection alarm device just described may be set at a higher alarm level than the 2000 ppm indicated above.

TABLE 1

| No. | Coating layer | Percent change in resistance | | |
|---|---|---|---|---|
| | | methane | hydrogen | ethanol |
| 1 | None | −21 | −82 | −86 |
| 2 | Single layer of $Cu_2O$ | −29 | −73 | −65 |
| 3 | Single layer of CuO | −31 | −76 | −71 |
| 4 | $SnO_2$ (n-type) on $LaNiO_2$ (p-type) | −51 | −37 | −23 |
| 5 | $Ta_2O_5$ (n-type) on $LaNiO_2$ | −48 | −41 | −32 |
| 6 | $SnO_2$ on NiO (p-type) | −56 | −32 | −18 |
| 7 | $SnO_2$ on $Mn_{1.5}CoNi_{0.5}O_4$ (p-type) | −42 | −44 | −35 |
| 8 | $SnO_2$ on $NiAl_2O_4$ (p-type) | −45 | −42 | −31 |
| 9 | $WO_3$ (n-type) on NiO (p-type) | −47 | −36 | −22 |
| 10 | ZnO (n-type) on NiO | −52 | −29 | −18 |
| 11 | $Fe_2O_3$ (n-type) on $LaNiO_3$ | −51 | −39 | −24 |
| 12 | $TiO_2$ (n-type) on NiO | −53 | −28 | −17 |
| 13 | $Nb_2O_5$ (n-type) on NiO | −54 | −37 | −32 |
| 14 | NiO on $SnO_2$ on NiO | −61 | −29 | −15 |
| 15 | $SnO_2$ and NiO on $SNO_2$ on NiO | −64 | −25 | −12 |

EXAMPLE 2

Example 1 describes an embodiment of the present invention consisting of a gas detector with a high sensitivity to methane gas in which the n-type oxide semiconductor $SnO_2$ is used as the gas sensing material. The present example describes another embodiment of the present invention in which a different n-type oxide semiconductor, ZnO, is used as the gas sensing material.

The gas detector in this embodiment has the same structure as the embodiment shown in FIGS. 1 and 2, and is fabricated by the same process, the only difference being the use, in step (4) described above of a gas sensing material comprising 89%, by weight, of ZnO powder, 1% palladium powder, and 10% PbO—TiO_2—SiO_2 glass. Tests were again conducted, under the same conditions as in Example 1, on the gas detectors obtained by forming coating layers 5 and 6 provided on the surface of gas sensing material layer 3 from various oxide semiconductors. The results obtained are shown in Table 2 together with results for gas detectors not provided with coating layers.

TABLE 2

| No. | Coating layer | Percent change in resistance | | |
|---|---|---|---|---|
| | | propane | hydrogen | ethanol |
| 1 | None | −22 | −47 | −94 |
| 2 | $SnO_2$ on $LaNiO_3$ | −56 | −25 | −32 |
| 3 | $Ta_2O_5$ on $LaNiO_3$ | −52 | −30 | −41 |
| 4 | $SnO_2$ on NiO | −59 | −27 | −27 |
| 5 | $WO_3$ on NiO | −50 | −24 | −39 |
| 6 | ZnO on NiO | −53 | −18 | −37 |
| 7 | $Fe_2O_3$ on $LaNiO_3$ | −55 | −22 | −31 |
| 8 | $TiO_2$ on NiO | −56 | −19 | −25 |
| 9 | $Nb_2O$ 5 on NiO | −52 | −27 | −38 |

It is apparent from Table 2 that, compared with conventional gas detectors without coating layers, represented in data No. 1, the gas detectors according to the present invention that have coating layers comprised of p-type and n-type oxide semiconductors (data Nos. 2 to 9) have a greatly reduced detection sensitivity to hydrogen and ethanol gas, and a greatly increased detection sensitivity to propane gas. This shows that the selectivity to propane gas is improved. The gas detectors according to the embodiments to the present invention shown in Table 2 are therefore clearly suitable as propane gas detectors.

Figure 3:
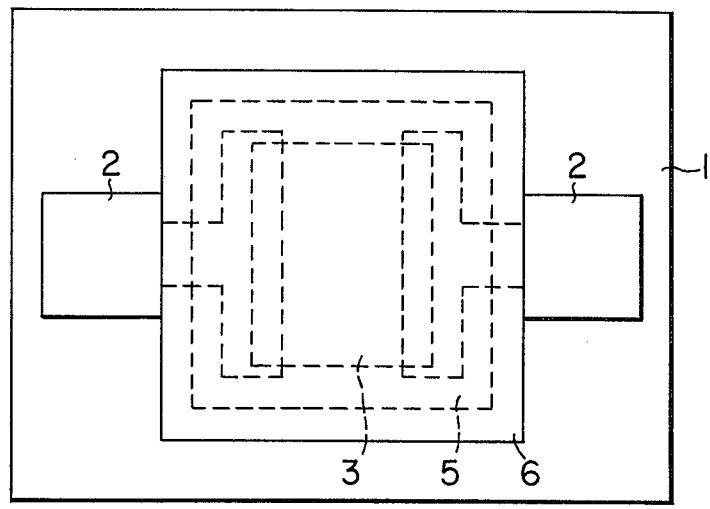
FIGS. 3 and 4 are plan and cross-sectional views of another embodiment of the gas detector in the present invention.
Figure 4:
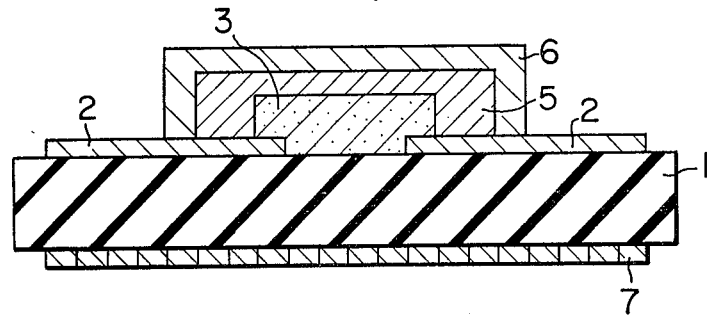

The sheet-type gas detector shown in FIGS. 3 and 4 differs from the sandwich-type gas detector shown in FIGS. 1 and 2 in that two opposing lower electrodes 2 are provided, eliminating the need for an upper electrode 4. Gas sensing material layer 3 is provided between the two opposing lower electrodes 2. Consequently, in the fabrication process for the gas detector shown in FIGS. 1 and 2, the step in which upper electrode 4 is formed becomes unnecessary, but in place of this, the two facing lower electrodes must be formed. This is the only difference in the fabrication process. In the present embodiment, a p-type oxide semiconductor comprising 89%, by weight, of NiO power, 1% palladium powder, and 10% PbO—TiO_2—SiO_2 glass was used as the gas sensing material. Tests were conducted on the gas detectors, shown in FIGS. 3 and 4, obtained by forming coating layers 5 and 6 provided on the surface of gas sensing material layer 3 from various oxide semiconductors, at an element temperature of about 300° C., other conditions being the same as in the tests for which results are shown in Tables 1 and 2. The results from these tests are shown in Table 3 together with the results for gas detectors not provided with coating layers.

TABLE 3

| No. | Coating layer | Percent change in resistance | | |
|---|---|---|---|---|
| | | hydrogen | ethanol | methane |
| 1 | None | +230 | +460 | 0 |
| 2 | NiO on $Fe_2O_3$ | +180 | +90 | 0 |
| 3 | $Co_3O_4$ on Zno | +130 | +110 | 0 |
| 4 | $LaNiO_3$ on $ZrO_2$ | +110 | +80 | 0 |

As is apparent from Table 3, compared to gas detectors without coating layers (data No. 1), gas detectors according to the present invention (data Nos. 2 to 4) that have coating layers 5 and 6 consisting of n-type and p-type oxide semiconductors have a greatly decreased detection sensitivity to ethanol gas. Because the detection sensitivity to hydrogen remains about the same, this clearly signifies increased selectivity for hydrogen gas. Hence, the gas detectors according to the embodiments of the present invention shown in Table 3 are clearly suited for use in the detection of hydrogen gas leaks in reduction furnaces and the like.

What is claimed is:

1. A gas detector which comprises a layer of gas sensing material comprising a p-type oxide semiconductor or an n-type oxide semiconductor, and at least one pair of coating layers comprising a layer containing a p-type oxide semiconductor and a layer containing an n-type oxide semiconductor provided in a multilayer arrangement on the surface of said layer of gas sensing material that contacts the gas, wherein when the gas sensing material comprises a p-type oxide semiconductor, the at least one pair of coating layers is formed in the order of a coating layer containing an n-type oxide semiconductor followed by a coating layer containing a p-type oxide semiconductor and when the gas sensing material comprises an n-type oxide semiconductor, the at least one pair of coating layers is formed in the order of a coating layer containing a p-type oxide semiconductor following by a coating layer containing an n-type oxide semiconductor.

2. A gas detector according to claim 1 wherein the p-type oxide semiconductor in the coating layer is selected from the group consisting of NiO, LaNiO$_3$, and the spinel-type material (Mn, Co, Ni, Al)$_3$O$_4$.

3. A gas detector according to claim 1 wherein the n-type semiconductor in the coating layer is selected from the group consisting of SnO$_2$, WO$_3$, Ta$_2$O$_5$, ZnO, Fe$_2$O$_3$, TiO$_2$, and Nb$_2$O$_5$.

4. A gas detector according to claim 1, wherein the p-type oxide semiconductor coating layer contains a p-type oxide semiconductor selected from a group consisting of NiO, LaNiO$_3$, and a spinel-type material (Mn, Co, Ni, Al)$_3$O$_4$; the n-type oxide semiconductor coating layer contains an n-type oxide semiconductor selected from the group consisting of SnO$_2$, WO$_3$, Ta$_2$O$_5$, ZnO, Fe$_2$O$_3$, TiO$_2$ and Nb$_2$O$_5$; and the gas sensing material contains an oxide semiconductor selected from the group consisting of SnO$_2$, ZnO and NiO.

5. A gas detector according to claim 1, wherein said gas sensing material comprises an n-type oxide semiconductor.

6. A gas detector according to claim 5, wherein a coating layer containing a p-type oxide semiconductor is formed on the surface of said layer of gas sensing material, and a coating layer containing an n-type oxide semiconductor is formed on said coating layer containing said p-type oxide semiconductor.

7. A gas detector according to claim 1, wherein said gas sensing material comprises a p-type oxide semiconductor.

8. A gas detector according to claim 7, wherein a coating layer containing an n-type oxide semiconductor is formed on the surface of said layer containing gas sensing material, and a coating layer containing a p-type oxide semiconductor is formed on said coaing layer of said n-type oxide semiconductor.

9. A gas detector according to claim 6, wherein alternating successive pairs of coating layers containing said p-type and n-type oxide semiconductors are provided in a multilayer arrangement on said coating layer containing an n-type oxide semiconductor.

10. A gas detector according to claim 8, wherein alternating successive pairs of coating layers containing said n-type and p-type oxide semiconductors are provided in a multilayer arrangement on said coating layer containing a p-type oxide semiconductor.

11. A gas detector according to claim 1, wherein the layer containing the gas sensing material also contains platinum metal and PbO—TiO$_2$—SiO$_2$ glass.

12. A gas detector according to claim 1, wherein the coating layer containing the p-type oxide semiconductor also contains PbO—TiO$_2$—SiO$_2$ glass.

13. A gas detector according to claim 1, wherein the coating layer containing the n-type oxide semiconductor also contains PbO—TiO$_2$—SiO$_2$ glass.

* * * * *